(12) United States Patent
Lowinger

(10) Patent No.: US 11,179,225 B2
(45) Date of Patent: Nov. 23, 2021

(54) PROTECTIVE DEVICE FOR USE IN ORAL SURGICAL PROCEDURES

(71) Applicant: ESSENTIAL SURGICAL PTY LTD, Bondi Junction (AU)

(72) Inventor: David Lowinger, Bondi Junction (AU)

(73) Assignee: ESSENTIAL SURGICAL PTY LTD, Bondi Junction (AU)

( * ) Notice: Subject to any disclaimer, the term of this patent is extended or adjusted under 35 U.S.C. 154(b) by 0 days.

(21) Appl. No.: 15/580,599

(22) PCT Filed: Jun. 10, 2016

(86) PCT No.: PCT/AU2016/000195
§ 371 (c)(1),
(2) Date: Dec. 7, 2017

(87) PCT Pub. No.: WO2016/197179
PCT Pub. Date: Dec. 15, 2016

(65) Prior Publication Data
US 2018/0168773 A1 Jun. 21, 2018

(30) Foreign Application Priority Data

Jun. 10, 2015 (AU) .............................. 2015902167

(51) Int. Cl.
*A61C 5/90* (2017.01)
*A61C 17/10* (2006.01)
(Continued)

(52) U.S. Cl.
CPC ................ *A61C 5/90* (2017.02); *A61B 18/00* (2013.01); *A61B 90/04* (2016.02); *A61C 17/08* (2019.05); *A61C 17/10* (2019.05); *A61B 17/02* (2013.01); *A61B 2018/00321* (2013.01); *A61B 2218/008* (2013.01)

(58) Field of Classification Search
CPC ......... A61C 5/90; A61C 17/043; A61C 17/02; A61B 90/04; A61B 18/00; A61B 2018/00321; A61B 2218/008
See application file for complete search history.

(56) References Cited

U.S. PATENT DOCUMENTS 3,772,790 A    11/1973  Swan
4,562,832 A *   1/1986  Wilder ..................... A61B 1/32
                                                138/DIG. 8
(Continued)

OTHER PUBLICATIONS

International Search Report for PCT/AU2016/000195, dated Sep. 23, 2016.
(Continued)

*Primary Examiner* — Tessa M Matthews
(74) *Attorney, Agent, or Firm* — Stephen J. Weyer, Esq.; Stites & Harbison, PLLC

(57) ABSTRACT

A protection device for use in oral surgery. The device comprises; a body having a first part which locates outside a patient's mouth and a second part which, during use, locates inside the mouth. The body is arranged such that at least a part of the body is resiliency deformable to enable manual shaping to accommodate an anatomical shape of at least part of a patient's mouth, thereby providing a physical barrier between surgical instrumentation and a patient's soft tissue.

24 Claims, 5 Drawing Sheets

(51) Int. Cl.
*A61C 17/08* (2006.01)
*A61B 90/00* (2016.01)
*A61B 18/00* (2006.01)
*A61B 17/02* (2006.01)

(56) References Cited

U.S. PATENT DOCUMENTS

| | | | |
|---|---|---|---|
| 4,889,490 A | 12/1989 | Jenkinson | |
| 4,947,829 A * | 8/1990 | Bullard | A61B 1/267 |
| | | | 600/101 |
| 5,152,300 A * | 10/1992 | Horst | A61C 5/90 |
| | | | 128/857 |
| 5,566,684 A | 10/1996 | Wagner | |
| 6,213,772 B1 * | 4/2001 | Costello | A61C 17/043 |
| | | | 433/140 |
| 8,852,169 B2 * | 10/2014 | Milo | A61C 17/08 |
| | | | 604/540 |
| 2005/0074720 A1 * | 4/2005 | Anderson | A61C 17/043 |
| | | | 433/136 |
| 2008/0064001 A1 | 3/2008 | Dorfman et al. | |
| 2008/0318183 A1 * | 12/2008 | Suzman | A61C 17/04 |
| | | | 433/93 |
| 2010/0119989 A1 * | 5/2010 | Raybuck | A61C 5/90 |
| | | | 433/93 |
| 2010/0268279 A1 * | 10/2010 | Gabelberger | A61B 17/7035 |
| | | | 606/278 |
| 2012/0167897 A1 | 7/2012 | Bettega | |
| 2013/0230822 A1 | 9/2013 | Hines et al. | |
| 2014/0212838 A1 * | 7/2014 | Nguyen | A61C 17/04 |
| | | | 433/92 |
| 2015/0093716 A1 * | 4/2015 | Fulton, III | A61C 17/043 |
| | | | 433/93 |
| 2015/0335409 A1 | 11/2015 | Hirsch | |
| 2020/0352680 A1 * | 11/2020 | Nguyen | A61C 17/08 |

OTHER PUBLICATIONS

Written Opinion of the International Searching Authority for PCT/AU2016/000195, completed Sep. 23, 2016.

* cited by examiner

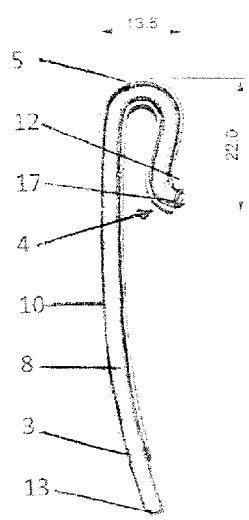
FIGURE 4
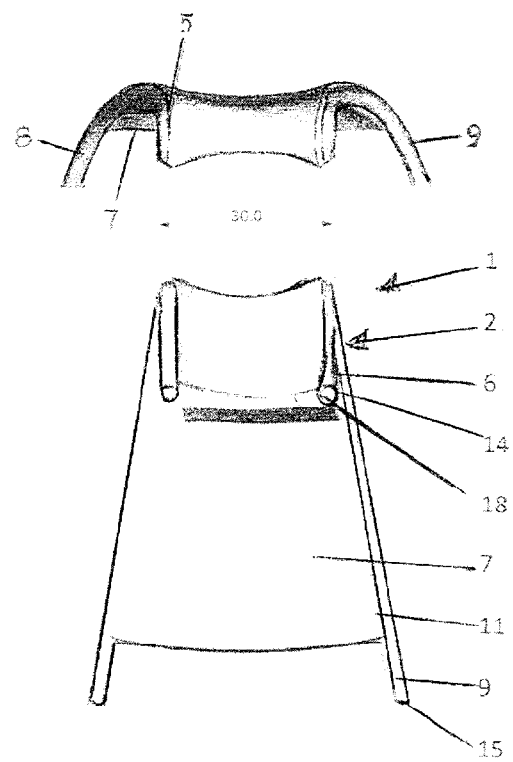
FIGURE 6
FIGURE 5

PROTECTIVE DEVICE FOR USE IN ORAL SURGICAL PROCEDURES

BACKGROUND

The present invention relates to surgical aids, tools and appliances and more particularly, relates to a device for use as a surgical aid to increase the safety of both patient and medical staff during surgery. More particularly the invention relates to a device which protects oral tissues from burns and other potential damage which may be occasioned during oral surgery. More particularly the present invention provides a disposable guard which protects the soft tissues of a patient during surgery of the oral cavity. The invention according to one embodiment further provides in the device a passage for evacuation of noxious or toxic fumes and gases which are generated when soft tissue is divided by a diathermy knife. The invention further relates to a surgical kit including a range of disposable devices of various sizes to accommodate different patients and which each protect oral tissues from the burns and other potential damage.

PRIOR ART

Oral surgery involves many procedures which include those performed on upper airways, tonsillectomy, adenoidectomy, palate surgery, tongue surgery, other transoral surgery, and certain dental procedures.

Upper airway surgery such as adenoidectomy and tonsillectomy are very commonly performed procedures on both children from 6 months old up to adults. Over the last 10 years there has been an increasing trend to use "hot" instruments such as diathermy (mono-polar electro-cautery), coblation (bipolar electro-cautery) and LASER to dissect or remove tissue to minimize blood loss compared to old fashion scalpel techniques. The use of "hot instruments is now the standard and universal method. These instruments have a handle held by the surgeon, a shaft through which the current flows and a tip through which the electricity is applied to the tissue. The shaft has a thin layer of insulation.

There are two significant problems which are occasioned by the use of hot instruments such as a diathermy. The first is the risk of burning soft tissue causing patient trauma and scarring. The second is the emission of toxic gases and other noxious agents such as viruses. The risks to patients and theatre staff arising from the use of these "hot" instruments can be summarised as follows:

Burns to the Corners of the Mouth.

This is a potentially devastating cosmetic and functional injury and can occur from heat transmitted through the shaft of the instrument. Faulty insulation in the shaft can lead to a direct electrical burn. Electricity passing/arcing to another instrument held against the corner of the mouth, can occur in the mouth (such as the metal sucker held by an assistant nurse).

Ignition of built up anaesthetic gases/oxygen in the mouth can also cause a flash fire.

Smoke Plume/Vapour.

a) Smoke filling the mouth/nose obstructing the view of the surgical site can slow down the operation and may impede an accurate dissection;

b) Smoke emitted from the mouth breathed in by surgeons, nurses, and an anaesthetist which also has occupational health and safety implications. A generated smoke plume may contain potentially infective, lethal and carcinogenic viruses which have been shown to exist in diathermy smoke.

Burns

The shaft of a diathermy can become hot enough from transmitted heat during prolonged use in a procedure enough to burn soft tissues. There have been many reported cases of faulty insulation allowing electricity to emit from the shaft. During oral surgery using a diathermy, burning tissue causes an emission of a large plume of smoke which can potentially contain and carry viruses such as CJD, HPV, HIV etc as well as toxins which are the equivalent of smoking a packet of cigarettes per hour of exposure. Although the known dissection instrument has now changed to a "hot" dissector, the rest of the instruments and techniques have not changed or adapted from the time of "cold steel" dissection.

During oral surgery, a patient's mouth is held open for access to the surgical site. According to known methodology, a patient's mouth is held open by a Boyle-Davis gag. This holds the mouth open wide along a Y axis but offers little protection for the facial and mouth tissues and particularly for the corners of the mouth. The instruments are passed into the mouth with the shaft of the instrument lying against the corners of the mouth as the mouth is a confined space. Currently the corners of the mouth are not adequately protected during surgery. Some make-shift protection is offered by use of gauze squares folded up and draped about the corners of the mouth. Since this affords inadequate protection, the patient's tissue can be burnt away. Mouth burns during tonsillectomy is known in the medical literature. Burns around the lips and mouth—primarily from the use of a cauterizing device—are an underreported complication of tonsillectomy and can result in long-term problems, according to a study reported in the Archives of Otolaryngology and Head and Neck Surgery. Removal of the tonsils (along with the nearby adenoid glands) "remains one of the most commonly performed surgical procedures in the United States., (Dr. Albert H. Park, of The University of Utah School of Medicine, Salt Lake City). While most patients do very well, a number of complications can occur, included bleeding, pain, and voice changes. In one study, a team conducted a review of children and teens who sustained a mouth burn during a tonsillectomy at Primary Children's Medical Center (PCMC) in Salt Lake City between January 1997 and December 2005. In addition, they conducted an online national survey of pediatric ear, nose, and throat doctors. Of the 4,327 surgeries performed at PCMC, 7 patients sustained mouth burns, including one that required reconstructive surgery. Of 298 surveys sent to physicians, 101 were completed. A total of 61 respondents reported having a patient develop a burn around the mouth. Roughly 10 percent of the burns were severe, necessitating additional treatment. Most of the burns occurred when the tonsils were removed with devices used to cauterize the area. However, a few cases occurred even when a scalpel was the main instrument for removal and cautery was simply used to control bleeding. The most common cause of injury was a defective cautery device tip. The surgeon's experience level, by contrast, had no impact on the risk of a mouth burn. The authors concluded that "because tonsillectomy remains one of the most frequently performed procedures, measures to avoid this complication exist and should be considered for every case.

[See: Archives of Otolaryngology and Head and Neck Surgery, January 2008.]

Permanent right corner of mouth and upper lip burn scars from tonsillectomy diathermy burn is a known risk of oral surgery, but there is little available to ensure that burns are prevented.

Toxic Gases

Currently gas emissions from burning tissue are arrested by a vacuum sucker which is held in the mouth by an assistant such as a theatre nurse. The sucker receives and evacuates the smoke that fills the mouth and obscures the surgeons view of the operating field. The surgeon's face (only covered by a thin mask) is very close to the patient's mouth. The nurse is also very close, so that both readily inhale smoke that emits during the procedure.

There are practical disadvantages arising from the use of the known equipment. For instance there is a need for nurse to stand for the duration of the surgery holding a sucker in the patient's mouth. This is laborious and tedious. It is also potentially dangerous as the sucker being waved in the mouth can damage teeth and other tissue. The sucker also obstructs the surgeon's view especially when operating in small mouths of infants. As uncuffed anaesthetic tubes are usually used for children, anaesthetic gases can leak into the mouth which, if not suctioned clear can be breathed in by and affect the surgeon and theatre personnel.

Accordingly, there is a long felt want to provide an insulation barrier to protect soft tissues from heat and burns during oral or dental surgeries. There is also a long felt want to provide an improved method of gas evacuation when soft tissues are burned during oral surgery.

INVENTION

Outlined broadly below are embodiments and features of the invention to enable the invention to be better understood, and in order that the present contribution to and improvement over the current the art may be better appreciated. There are, of course, additional features of the invention that will be described hereinafter and which will form the subject matter of the claims.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways in various anatomical sites including in veterinary applications. Also, it is to be understood that the phraseology and terminology employed herein are for the purpose of description and should not be regarded as limiting. As such, those skilled in the art will appreciate that the conception, upon which this disclosure is based, may readily be utilized as a basis for the designing of other variations on the tool assembly, structures, methods and systems for carrying out the purposes of the present invention.

It is therefore an object of the present invention to provide a new and improved tool which removes the practical disadvantages encountered in oral surgery With the aforesaid prior art problems and disadvantages of current methodologies, the present invention provides improvement in devices used in oral surgery and more particularly provide a disposable soft tissue protector which protects such structures as corners of the mouth during surgery. More particularly the invention provides a device which protects oral tissues from burns and other potential damage which may be occasioned during oral surgery. More particularly the present invention provides a disposable guard which protects the soft tissues of a patient during surgery of the oral cavity and is capable of receiving and evacuating gasses created by hot instruments.

In one broad form the present invention comprises: a protection device for use in oral surgery, the device comprising a body having a first part which locates outside the mouth and a second part which during use, locates inside the mouth, the device body arranged such that at least a part of the body is resiliently deformable to enable manual shaping to accommodate an anatomical shape of at least part of a patient's mouth, thereby providing a physical barrier between surgical instrumentation and a patient's soft tissue.

According to one embodiment, the protection device comprises a malleable body which can be adjusted manually to accommodate different mouth shapes. Preferably, the body defines a substantially U shaped configuration which can be plied by the surgeon or operator to suit the anatomical mouth geometry of a particular patient. According to a further embodiment, the device includes at least one tube having a first end which is adapted to receive and retain a known discharge tube to discharge said gaseous products to a collection receptacle or to the outside air and a second end which locates inside the mouth. The second end has an opening which receives gaseous effluent from such sources as diathermy burning. According to one embodiment the suction tubes are integral with the body of the device. According to an alternative embodiment the suction tubes are detachably attached to the body of the device.

Preferably the body of the device is manufactured from materials selected from plastics, metals or a combination of the two. The device may be manufactured from other materials which are preferably pliable or plastic, electrically insulating and thermally inert. In an alternative embodiment the protection device is manufactured from a material or material combination which is not intended for user adjustment and is pre set to accommodate a patient's mouth. In this regard the device is capable of self locating and remaining connected to the mouth of a patient, protecting such areas as the corner of the mouth and lips. The design geometry can be varied to suit different anatomical sizes enabling staff to select a size suitable for a particular patient. Typically a surgeon will place a return portion over the lip margins and crimp it against the mouth using its inbuilt plasticity. According to one embodiment, a kit of protection devices can be provided allowing a surgeon to select a suitable size for a particular patient anatomy.

In another broad form the present invention comprises: a protection device for use in oral surgery, the device comprising a body having a first distal part which locates outside the mouth of a patient and a second part which during use, locates inside the mouth, the device body including a return which is deformable to engage and accommodate the shape of a patient's lips thereby providing a physical barrier between surgical instrumentation and a patient's soft tissue.

In another broad form the present invention comprises: a protection device for use in oral surgery, the device comprising a body having a first distal part which locates outside the mouth of a patient and a second part which during use, locates inside the mouth, the device body including a return which is deformable to engage and accommodate the shape of a patient's lips thereby providing a physical barrier between surgical instrumentation and a patient's soft tissue; the device further comprising at least one tube extending at least from the first end to the second end, the first end adapted to receive a suction tube to remove gases entering said second end.

In one broad form, the present invention comprises: a protection device for use in oral surgery, the device comprising a body having a first part which locates outside the mouth and a second part which during use, locates inside the mouth, the device body arranged such that at least a part of the body conforms to the an anatomical shape of at least part of a patient's mouth, the body providing a physical barrier between surgical instrumentation and a patient's soft tissue.

In another broad form the present invention comprises: a protection device for use in oral surgery, the device comprising a body having a first part which locates outside a patient's mouth and a second part which, during use, locates inside the mouth, the device body arranged such that at least a part of the body is resiliently deformable to enable manual shaping to accommodate an anatomical shape of at least part of a patient's mouth, thereby providing a physical barrier between surgical instrumentation and a patient's soft tissue.

According to one embodiment the planar region arranged to oppose an adjacent inside surface of the mouth and the device body is malleable/pliable enable adjustability to accommodate different mouth shapes. A majority of the body of the device is located inside the mouth and a minority of the body extends outside the mouth. The body has a return portion through which the body transitions from the planar region inside the mouth to a cheek engagement portion outside the mouth via a return portion which is substantially U shaped. The substantially U shaped formation is adjustable to suit the anatomical mouth geometry of a particular patient. The protection device includes at least one through passage extending from a location inside the mouth to a location outside the mouth and along the body of the device.

Each through passage is each formed by at least one tube each one having a first end disposed outside the mouth and a second end disposed inside the mouth. The protection device has a planar region and an integrally connected face engagement portion formed from the same material and each having common side edges. Preferably there are two tubes one of each locating along each side edges. The first end of the tube is adapted to receive and retain a discharge tube which locates outside the mouth, to enable discharge of gaseous products from inside the mouth to a collection receptacle or to the outside air. The second end of each tube has an opening which receives gaseous effluent created inside the mouth from such sources as diathermy burning. The tubes act as suction tubes which are detachably attached to the side edges of the body of the device.

Preferably, the body of the device is manufactured from materials selected from plastics, metals or a combination of the two. The device is preferably manufactured from materials which are pliable and plastic, electrically insulating and thermally inert. The device is capable of self locating and remaining connected to the mouth of a patient, protecting such areas as the corner of the mouth and lips. The shape of the device can be varied to suit different anatomical sizes enabling staff to select a size suitable for a particular patient. The device has inbuilt plasticity to enable a surgeon to crimp the device over at least a portion of lip margins. According to one embodiment, the device is manufactured from a rigid material or combination of materials which are non pliable and pre set to accommodate a particular patient's mouth.

In another broad form the present invention comprises: a protection device for use in oral surgery, the device comprising a body having a first end which locates, during use, outside the mouth of a patient and a second end which locates inside the mouth, the device body including a return portion which is deformable to engage and accommodate the shape of at least part of a patient's lips, thereby providing a physical barrier between surgical instrumentation and a patient's soft tissue which extends from the inside to the outside the patent's mouth. According to a preferred embodiment, the device includes at least one discharge tube each including a through passage which allows transmission of gas induced during surgery from inside the mouth to the outside of the mouth. A first end is adapted to receive a suction tube to remove gases entering via said second end. The suction tube clears the mouth of smoke plume and gases via said at least one discharge tube to ensure a clear view of an oral surgical field and to minimize the emission of surgically induced smoke.

According to the preferred embodiment, the device minimises risks of tissue burning and gas ingestion in oral surgeries by 1. protecting the side of the mouth from thermal/electrical injury; and 2. providing continuous suction to clear the mouth of smoke plume and gases to ensure a clear view, minimize the emission of smoke to the surgeon and staff and to negate the need for an oral sucker and a nurse to hold it.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

The present invention provides an alternative to the known prior art and the shortcomings identified. The foregoing and other objects and advantages will appear from the description to follow. In the description reference is made to the accompanying representations, which forms a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying illustrations, like reference characters designate the same or similar parts throughout the several views. The following detailed description is, therefore, not to be taken in a limiting sense, and the scope of the present invention is best defined by the appended claims.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 4 shows a side elevation view of the protector of FIG. 1.

FIG. 5 shows a front elevation view of the protector of FIG. 1.

FIG. 6 shows a top elevation view of the protector of FIG. 1.

DETAILED DESCRIPTION

The present invention will now be described in more detail according to a preferred embodiment but non limiting embodiment and with reference to the accompanying illustrations. The examples referred to herein are illustrative and are not to be regarded as limiting the scope of the invention. While various embodiments of the invention have been described herein, it will be appreciated that these are capable of modification, and therefore the disclosures herein are not to be construed as limiting of the precise details set forth, but to avail such changes and alterations as fall within the purview of the description.

Figure 1:
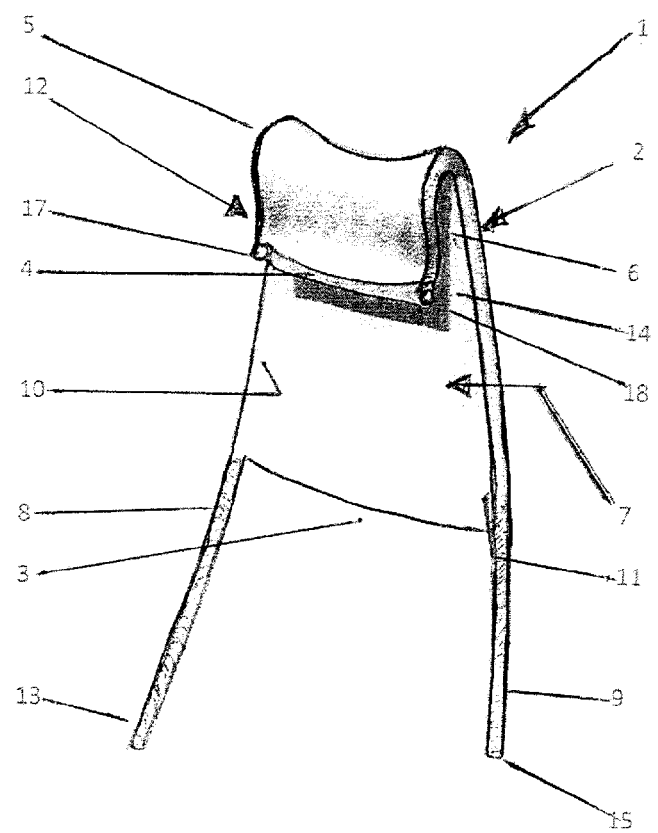
FIG. 1 shows a perspective view of a mouth protector according to a preferred embodiment.

FIG. 1 shows a perspective view of a mouth protecting device 1 according to a preferred embodiment. Protector 1 comprises a body 2 having a first end 3 and second end 4. Second end 4 locates inside the mouth of a patient (not shown) and first end 3 locates outside the mouth of a patient with return portion 5 defining a recess 6 which accommodates and wraps around the lips of the patient. Return portion 5 according to one embodiment, resiliently deformable and/or pliable and allows a surgeon to adjust to accommodate the patient's lip. Body 2 includes a planar region 7 which, when device 1 is in use, lies against the outside of the patient's cheek and provides protection while the mouth is held open during surgery, a physical barrier between surgical instrumentation such as a hot diathermy and the cheek and to some extent the buccal region.

Protector 1 includes tubes 8 and 9 adapted to respective edge regions 10 and 11 of body 2. These may be integrally formed with body 2 or alternatively connected to body 2 depending upon particular design requirements and selected materials of construction. Tubes 8 and 9 are joined to a vacuum line which evacuates gases from the surgical field (see FIG. 8). Tube 8 has a first end 12 which when device 1 is in use locates inside a mouth of a patient and a second end 13 which terminates outside the mouth. Likewise tube 9 has a first end 14 which, when device 1 is in use, locates inside a mouth of a patient and a second end 15 which terminates outside the mouth. According to one embodiment, tubes 8 and 9 each include respective through passages 17 and 18 which provide a suction paths to evacuate the toxic gases which accumulate at the site of the oral surgery. Ends 13 and 15 engage a gas discharge tube (see FIG. 8).

Figure 2:
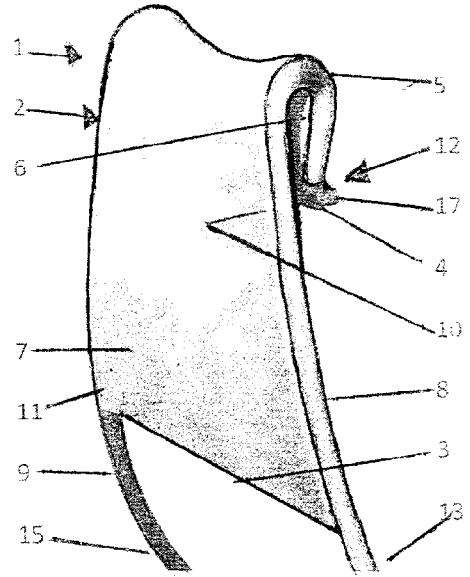
FIG. 2 shows a rear perspective view the protector of FIG. 1.

FIG. 2 shows with corresponding numbering a rear perspective view of the protector 1 of FIG. 1.

Figure 3:
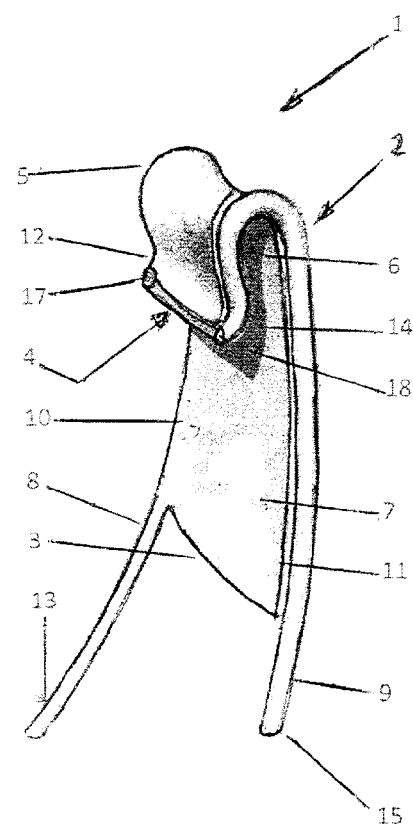
FIG. 3 shows an opposite side perspective view of the protector of FIG. 1.

FIG. 3 shows with corresponding numbering a side perspective view of the protector of FIG. 1.

FIG. 4 shows a side elevation view of the protector of FIG. 1.

FIG. 5 shows a front elevation view of the protector of FIG. 1.

FIG. 6 shows a top elevation view of the protector of FIG. 1.

Figure 7:
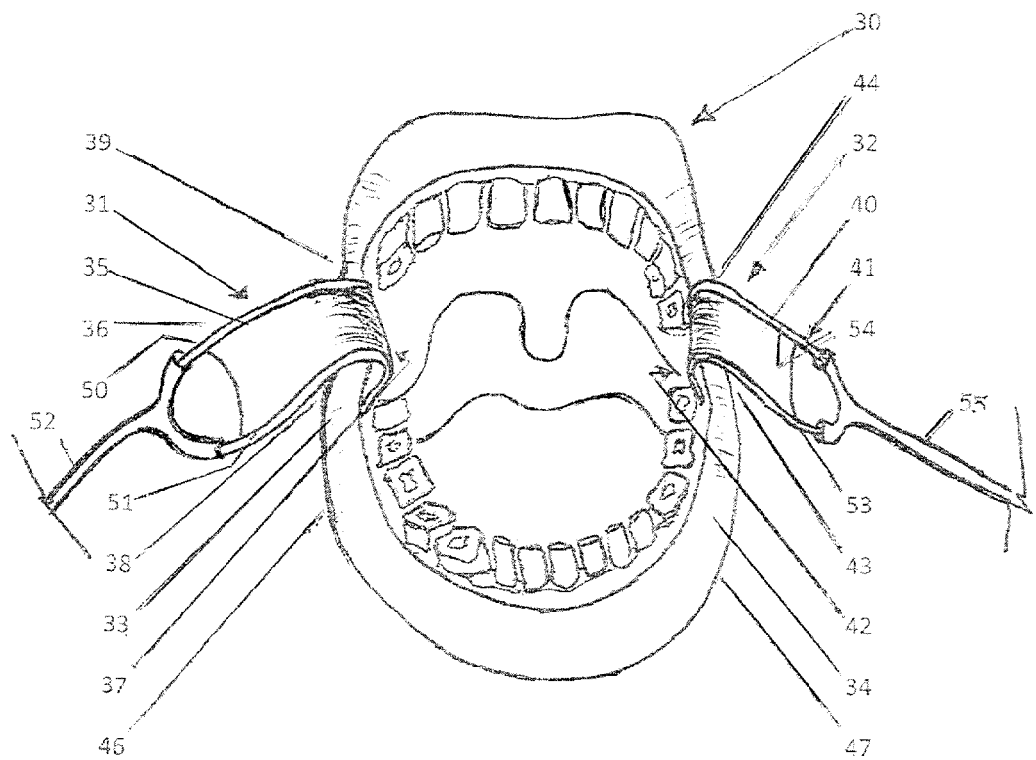
FIG. 7 shows a plan view of an open mouth of a patient with a protection device used either side of the mouth engaging the lips.

FIG. 7 shows a plan view of an open mouth 30 of a patient with a first protection device 31 and opposing second device 32 respectively engaging lip regions 33 and 34. Protector 31 comprises a body 35 having a first end 36 and second end 37. Second end 37 locates inside the mouth 30 and receives lip region 33 in recess 38 defined by radiused return 39. Likewise protector 32 comprises a body 40 having a first end 41 and second end 42. Second end 42 locates inside the mouth 30 and receives lip region 34 in recess 43 defined by radiused return 44. Return portions 39 and 44 are according to one embodiment, resiliently deformable and/or pliable and allow a surgeon to adjust to accommodate the patient's lip regions 33 and 34 respectively. Body 35 of device 31 and body 40 of lie against and protect cheeks 46 and 47 respectively and provide a physical barrier to unwanted instrument contact with the patient.

Protection device 31 includes tubes 50 and 51 adapted to respective edge regions of body 35. Tubes 50 and 51 are joined to a vacuum line 52 which evacuates gases away from the surgical field to a collection unit or other known collector. Likewise, protection device 32 includes tubes 53 and 54 adapted to respective edge regions of body 40. Tubes 53 and 54 are joined to a vacuum line 55 which also evacuates gases away from the surgical field to a collection unit or other known collector. Although the arrangement in FIG. 7 employs bi lateral opposing like devices, it will be appreciated by persons skilled in the art that the following combinations can also be employed: one device without gas evacuation tubes, one device with gas evacuation tubes, two devices but only one with gas evacuation tubes.

Figure 8:
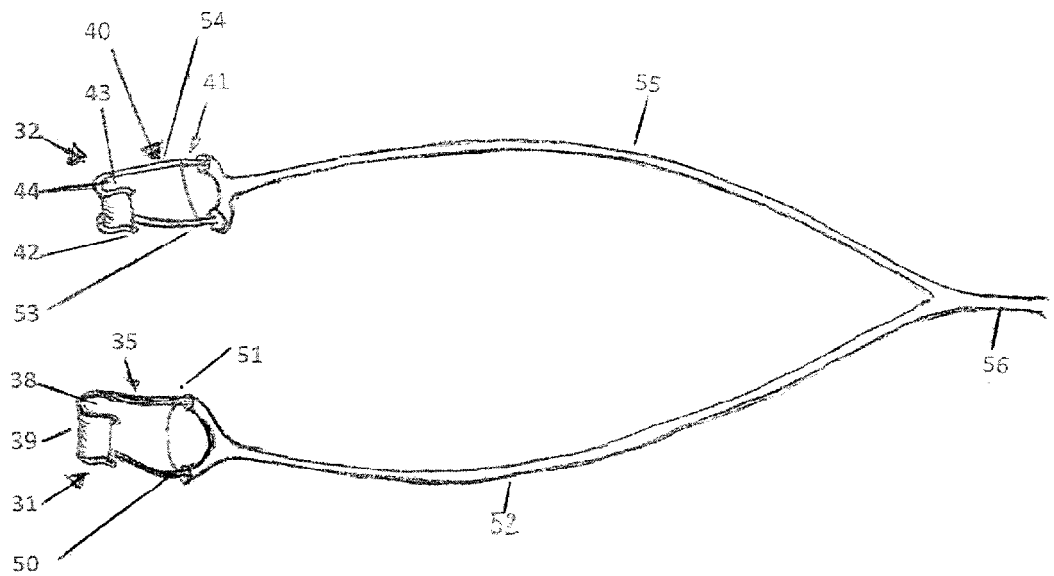
FIG. 8 shows the protection devices of FIG. 8 each connected to a gas discharge tube.

FIG. 8 shows with corresponding numbering, the protection devices 31 and 32 of FIG. 8 each connected to respective vacuum discharge lines 52 and 55 which both terminate in a single line 56 en route to the gas collection apparatus (not shown).

Figures 9, 10:
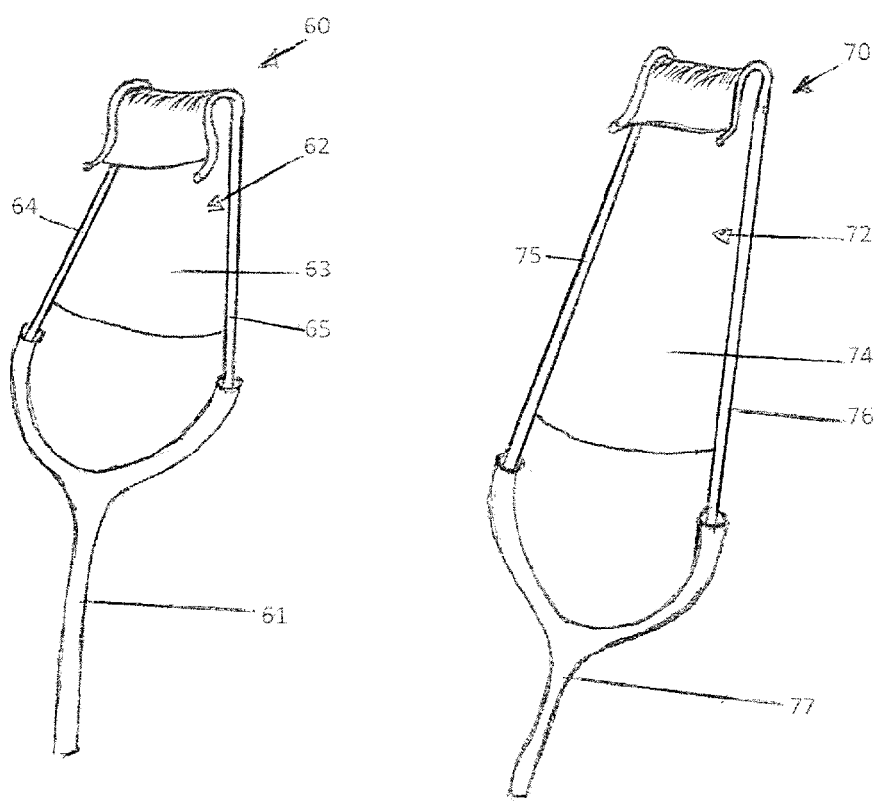
FIG. 9 shows a perspective view of a smaller version of a protective device according to one embodiment.
FIG. 10 shows a more elongated version of a protective device according to another embodiment.

FIG. 9 shows a perspective enlarged view of a smaller version of a protective device 60 according to one embodiment connected to a vacuum tube 61. Protector 60 comprises a body 62 including a planar region 63 and tubes 64 and 65 preferably integrally formed with body 62. Tubes 64 and 65 are joined to vacuum line 61 which evacuates gases from the surgical field (see FIG. 8).

FIG. 10 shows a more elongated version of a protective device 70 according to another embodiment. Protector 70 comprises an elongated body 72 including a planar region 74 having significantly increased surface area and elongated evacuation tubes 75 and 76. Tubes 75 and 76 are joined to vacuum line 77 which evacuates gases from the surgical field.

The vacuum tubes preferably enter the mouth to a depth as far as possible. The mid tube lengths of the vacuum tubes are preferably around 500 mm long and are press fit into a Y shaped joiner. Preferably the width of the lip protector moulding and tube would be in the region of 25-30 mm but other sizes are contemplated to accommodate different sized patient anatomies.

According to one embodiment, the device is constructed flat with built in capacity for bending into shape by a user. The pliability may be introduced using an internal membrane in the body. In a further embodiment, the protection device comprises a moulded silicone body which is contoured to slide over a patient's lip and clamp lightly on walls of the cheek. The clamping force can be adjusted by the surgeon when locating the device on the patient's mouth. Incorporated in the moulded silicone are tubes which have a first end which locates in the mouth when the device is in situ and a second end extending outside the mouth. Each tube has a through passage which spans between the first and second ends. The tubes have an inside diameter within the range of 2 mm-5 mm and an outside diameter within the range of 3 mm-7 mm. A preferred tube size is 2 mm inside diameter and 3.2 mm outside diameter. Preferably the tubes are clear and either bonded to guide channels or moulded integral with the body of the device.

According to a preferred embodiment the device is malleable and easily applied for self—retention in a corner-of-the-mouth. Preferably, during surgery there is provided one on each side of the patient's mouth. Preferably one or both of the devices include integral suction tubes incorporated into the body of the device with the tubes being connected to known standard suction tubing. The protection device preferably has a length within the range 25-75 mm but alternative sizes are contemplated. Materials of construction are selected from smooth, heat resistant, non reflective, semi-firm material, plastic/silastic or a coated thin malleable metal with a heat/electricity insulating coating. Selecting a malleable material allows the device to engage the lip region of the mouth and with sufficient clamping elasticity in the material to stay in place during surgery. This eliminates the need to use inefficient wet gauze squares which are currently in use and sit on the corners of the mouth.

Preferably the device is single use and disposable although materials capable of sterilization are contemplated. Although the embodiments shown incorporate two lateral suction tubes, alternative embodiments are contemplated, such as but not limited to, use of one suction tube, location of a tube or tubes intermediate the edges or a tube which can be attached as required to the protection device. As the suction is of a smoke plume, rather than fluid, the suction tubes/canulas do not need to be wide bore. The radii of curvature of the tubes and angles of repose are adapted to suit particular mouth geometry as required and to facilitate passage of gases. The suction tubing would preferably be around 30 cm long with an end able to be attached to standard suction tubing. In a further embodiment, the suction tube includes a form of double adaptor so that theatre wall suction tubing can be used for both this device and a standard gas sucker. Typically the devices are provided in a sterile, disposable kit including those with and without suction tubes and adaptors as required. The device described herein improves patient safety and is convenient for staff application.

It will be appreciated by those skilled in the art that numerous variations and modifications may be made to the invention without departing from the overall spirit and scope of the invention broadly described herein.

The claims defining the invention are as follows:

1. A mouth protection device for use during oral surgery, the device comprising;
   a device body having;
   a first planar sheet part which during use, locates outside a patient's mouth and opposes a patient's outer cheek;
   a second planar sheet part which, during use, locates inside the mouth and opposes an inside surface of the cheek; the second part abbreviated relative to the first part such that its length is less than an overall length of the first part;
   a third part between the first and second planar sheet parts of the device body which is resiliently deformable and forms a recess to accommodate an anatomical shape of at least part of a patient's lips, thereby providing a physical barrier between surgical instrumentation and a patient's soft tissue; the device body including a plurality of suction tubes each one having a first free open end configured to locate outside the mouth and a second open free end configured to locate inside the mouth; each of said tubes extending along the body of the device from the second part to the first part via the third part and each having a through passage extending along the device body from the second end to the first end.

2. The device according to claim 1 wherein the second planar sheet part is abbreviated such that its longitudinal extent is less than the length of the longitudinal extent of the first planar sheet part.

3. The protection device according to claim 2, wherein the third part comprises a return portion through which the device body is configured to transition from the first part outside the patient's mouth to the second part inside the patients mouth.

4. The protection device according to claim 3, wherein the return portion is a substantially U shaped formation.

5. The protection device according to claim 4, wherein a minority of the body forming the second planar part of the device is configured to locate inside the mouth and a majority of the body forming the first planar part is configured to extend outside the mouth.

6. The protection device according to claim 5, wherein the return portion is configured to envelope a mouth corner and at least part of lips of a patient.

7. The protection device according to claim 6, wherein the device body is malleable to accommodate different mouth corner and lips contours of patients.

8. The protection device according to claim 6, wherein the first and second parts of the device are manufactured from a rigid material or combination of rigid materials which are non-pliable and the third part remains resiliently deformable to accommodate a particular patient's mouth.

9. The protection device according to claim 6, wherein the device is manufactured from a combination of pliable/deformable material or combination of materials which are user adjustable to accommodate a particular patient's mouth.

10. The protection device according to claim 7, wherein the substantially U shaped return portion is made from a pliable material to enable said accommodation of different mouth corner and lips contours.

11. The protection device according to claim 10, wherein the second planar part is configured to locate inside the mouth and the first part has side edges symmetrical about a longitudinal axis.

12. The protection device according to claim 11, wherein the first open free end of each of said suction tubes is adapted to receive and retain a discharge tube which locates outside the mouth, to enable discharge via the discharge tubes of gaseous products from inside the mouth to a collection receptacle or to the outside air.

13. The protection device according to claim 12, wherein the second open free end of each of said suction tubes has an opening which is configured to receive gaseous effluent created inside the mouth from such sources as diathermy burning.

14. The protection device according to claim 13, wherein the suction tubes are attached to the side edges of the body of the device.

15. The protection device according to claim 14, wherein the suction tubes are detachably attached to the body of the device.

16. The protection device according to claim 15, wherein the body of the device is manufactured from materials selected from plastics, metals or a combination of the two.

17. The protection device according to claim 16, wherein the device is manufactured from materials which are pliable and plastic, electrically insulating and heat resistant.

18. The protection device according to claim 17, wherein the device is capable of self-location and remaining connected to the mouth of a patient, while protecting the corner of the mouth and lips.

19. The protection device according to claim 18, wherein the shape of the device can be varied to suit different anatomical sizes selection of a size suitable for a particular patient.

20. The protection device according to claim 19, wherein the device has inbuilt plasticity to enable a surgeon to locate the device over at least a portion of lip margins.

21. The protection device according to claim 20, wherein the device can be crimped against the mouth using the inbuilt plasticity.

22. The protection device according to claim 21, wherein the device is disposable.

23. The protection device according to claim 21, wherein the device is reusable.

24. The protection device according to claim 21, wherein the device is supplied as component of a kit of components.

\* \* \* \* \*